(12) United States Patent
Berez et al.

(10) Patent No.: US 12,310,884 B2
(45) Date of Patent: May 27, 2025

(54) THERAPEUTIC ORGAN COOLING (71) Applicant: PALMERA MEDICAL, INC., Mountain View, CA (US)

(72) Inventors: Aaron Berez, Mountain View, CA (US); Tina Ting Ye, Mountain View, CA (US); Elaine Lim, Mountain View, CA (US)

(73) Assignee: PALMERA MEDICAL, INC., Mountain View, CA (US)

( * ) Notice: Subject to any disclaimer, the term of this patent is extended or adjusted under 35 U.S.C. 154(b) by 0 days.

(21) Appl. No.: 17/958,407

(22) Filed: Oct. 2, 2022

(65) Prior Publication Data

US 2023/0028310 A1 Jan. 26, 2023

Related U.S. Application Data

(63) Continuation of application No. 16/594,112, filed on Oct. 7, 2019, now Pat. No. 11,464,671, which is a continuation of application No. PCT/US2018/026600, filed on Apr. 6, 2018.

(60) Provisional application No. 62/483,294, filed on Apr. 7, 2017.

(51) Int. Cl.
*A61F 7/12* (2006.01)
*A61B 17/00* (2006.01)
*A61F 7/00* (2006.01)
*A61M 25/10* (2013.01)

(52) U.S. Cl.
CPC .............. *A61F 7/123* (2013.01); *A61M 25/10* (2013.01); *A61B 2017/00292* (2013.01); *A61F 2007/0056* (2013.01); *A61F 2007/126* (2013.01)

(58) Field of Classification Search
CPC .............. A61F 7/123; A61F 2007/0056; A61F 2007/126; A61F 2007/0063; A61F 7/12; A61F 7/0085; A61M 25/10; A61B 2017/00292
See application file for complete search history.

(56) References Cited

U.S. PATENT DOCUMENTS

| | | |
|---|---|---|
| 3,712,306 A | 1/1973 | Bryne |
| 4,784,638 A | 11/1988 | Ghajar et al. |
| 4,821,716 A | 4/1989 | Ghajar et al. |
| 4,931,056 A | 6/1990 | Ghajar et al. |
| 4,998,938 A | 3/1991 | Ghajar |
| 5,180,387 A | 1/1993 | Ghajar |
| 5,496,271 A | 3/1996 | Burton et al. |
| 6,042,559 A | 3/2000 | Dobak |
| 6,096,068 A | 8/2000 | Dobak |

(Continued)

FOREIGN PATENT DOCUMENTS

| | | |
|---|---|---|
| CN | 202714918 U | 2/2013 |
| CN | 104254294 A | 12/2014 |

(Continued)

*Primary Examiner* — Jonathan T Kuo
(74) *Attorney, Agent, or Firm* — FisherBroyles, LLP; James W. Hill; Andrew K. Gonsalves (57) ABSTRACT

An organ can be cooled to minimize ischemic tissue damage from a vascular occlusion by a thrombus or dissection. A catheter including a thermal member can be used to introduce cold fluid downstream from an arterial occlusion to cool tissue affected by the occlusion. This is particularly useful to minimize neurologic damage from a thrombotic stroke.

15 Claims, 7 Drawing Sheets

(56) References Cited

U.S. PATENT DOCUMENTS

| | | |
|---|---|---|
| 6,149,677 A | 11/2000 | Dobak |
| 6,206,885 B1 | 3/2001 | Ghahremani et al. |
| 6,224,624 B1 | 5/2001 | Lasheras et al. |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,299,599 B1 | 10/2001 | Pham et al. |
| 6,312,452 B1 | 11/2001 | Dobak, III et al. |
| 6,325,818 B1 | 12/2001 | Werneth |
| 6,364,899 B1 | 4/2002 | Dobak, III |
| 6,379,378 B1 | 4/2002 | Werneth et al. |
| 6,383,210 B1 | 5/2002 | Magers et al. |
| 6,450,987 B1 | 9/2002 | Kramer |
| 6,464,716 B1 | 10/2002 | Dobak, III et al. |
| 6,468,296 B1 | 10/2002 | Dobak, III et al. |
| 6,471,717 B1 | 10/2002 | Dobak, III et al. |
| 6,475,231 B2 | 11/2002 | Dobak, III et al. |
| 6,478,811 B1 | 11/2002 | Dobak, III et al. |
| 6,478,812 B2 | 11/2002 | Dobak, III et al. |
| 6,482,226 B1 | 11/2002 | Dobak, III |
| 6,491,039 B1 | 12/2002 | Dobak, III |
| 6,491,716 B2 | 12/2002 | Dobak III et al. |
| 6,530,946 B1 | 3/2003 | Noda et al. |
| 6,533,804 B2 | 3/2003 | Dobak, III et al. |
| 6,540,771 B2 | 4/2003 | Dobak, III et al. |
| 6,551,309 B1 | 4/2003 | LePivert |
| 6,551,349 B2 | 4/2003 | Lasheras et al. |
| 6,558,412 B2 | 5/2003 | Dobak, III |
| 6,576,001 B2 | 6/2003 | Werneth et al. |
| 6,576,002 B2 | 6/2003 | Dobak, III |
| 6,582,455 B1 | 6/2003 | Dobak, III et al. |
| 6,585,752 B2 | 7/2003 | Dobak, III et al. |
| 6,595,967 B2 | 7/2003 | Kramer |
| 6,599,312 B2 | 7/2003 | Dobak, III |
| 6,602,276 B2 | 8/2003 | Dobak, III et al. |
| 6,607,517 B1 | 8/2003 | Dae et al. |
| 6,648,906 B2 | 11/2003 | Lasheras et al. |
| 6,648,908 B2 | 11/2003 | Dobak, III et al. |
| 6,660,028 B2 | 12/2003 | Magers et al. |
| 6,676,688 B2 | 1/2004 | Dobak, III et al. |
| 6,676,689 B2 | 1/2004 | Dobak, III et al. |
| 6,676,690 B2 | 1/2004 | Werneth |
| 6,679,907 B2 | 1/2004 | Dobak, III et al. |
| 6,685,732 B2 | 2/2004 | Kramer |
| 6,692,488 B2 | 2/2004 | Dobak, III et al. |
| 6,695,873 B2 | 2/2004 | Dobak, III et al. |
| 6,702,841 B2 | 3/2004 | Nest et al. |
| 6,702,842 B2 | 3/2004 | Dobak, III et al. |
| 6,719,723 B2 | 4/2004 | Werneth |
| 6,719,779 B2 | 4/2004 | Daoud |
| 6,726,708 B2 | 4/2004 | Lasheras |
| 6,740,109 B2 | 5/2004 | Dobak, III |
| 6,755,850 B2 | 6/2004 | Dobak, III |
| 6,786,218 B2 | 9/2004 | Dobak, III |
| 6,818,011 B2 | 11/2004 | Dobak, III |
| 6,830,581 B2 | 12/2004 | Magers |
| 6,843,800 B1 | 1/2005 | Dobak, III |
| 6,869,440 B2 | 3/2005 | Dobak, III |
| 6,887,262 B2 | 5/2005 | Dobak, III et al. |
| 6,905,494 B2 | 6/2005 | Yon et al. |
| 6,905,509 B2 | 6/2005 | Dobak, III et al. |
| 6,918,924 B2 | 7/2005 | Lasheras et al. |
| 6,974,463 B2 | 12/2005 | Magers et al. |
| 6,979,345 B2 | 12/2005 | Werneth |
| 6,991,645 B2 | 1/2006 | Dobak, III |
| 7,001,378 B2 | 2/2006 | Yon et al. |
| 7,004,960 B2 | 2/2006 | Daoud |
| 7,018,399 B2 | 3/2006 | Dobak, III et al. |
| 7,033,367 B2 | 4/2006 | Ghahremani et al. |
| 7,052,508 B2 | 5/2006 | Werneth |
| 7,063,718 B2 | 6/2006 | Dobak, III |
| 7,066,947 B2 | 6/2006 | Nest et al. |
| 7,066,948 B2 | 6/2006 | Dobak, III et al. |
| 7,094,253 B2 | 8/2006 | Dobak, III et al. |
| 7,101,386 B2 | 9/2006 | Dobak, III |
| 7,189,254 B2 | 3/2007 | Magers |
| 7,211,066 B1 | 5/2007 | Merrill |
| 7,211,105 B2 | 5/2007 | Magers et al. |
| 7,211,106 B2 | 5/2007 | Dobak, III et al. |
| 7,288,089 B2 | 10/2007 | Yon et al. |
| 7,288,109 B2 | 10/2007 | Yon et al. |
| 7,291,144 B2 | 11/2007 | Dobak, III et al. |
| 7,294,142 B2 | 11/2007 | Dobak, III et al. |
| 7,300,453 B2 | 11/2007 | Yon |
| 7,311,725 B2 | 12/2007 | Dobak, III |
| 7,351,254 B2 | 4/2008 | Magers |
| 7,371,254 B2 | 5/2008 | Dobak, III |
| 7,422,600 B2 | 9/2008 | Dobak, III |
| 7,449,018 B2 | 11/2008 | Kramer |
| 7,458,984 B2 | 12/2008 | Yon et al. |
| 7,491,223 B2 | 2/2009 | Lasheras |
| 7,651,518 B2 | 1/2010 | Dobak, III et al. |
| 7,704,220 B2 | 4/2010 | Solar et al. |
| 7,766,949 B2 | 8/2010 | Dobak, III et al. |
| 7,789,846 B2 | 9/2010 | Solar et al. |
| 7,850,723 B1 | 12/2010 | Magers |
| 7,914,564 B2 | 3/2011 | Magers et al. |
| 7,922,752 B2 | 4/2011 | Dobak, III et al. |
| 7,951,183 B2 | 5/2011 | Dobak, III |
| 7,998,182 B2 | 8/2011 | Dobak, III et al. |
| 8,038,703 B2 | 10/2011 | Dobak, III et al. |
| 8,043,283 B2 | 10/2011 | Dobak, III et al. |
| 8,043,351 B2 | 10/2011 | Yon et al. |
| 8,109,897 B2 | 2/2012 | Solar et al. |
| 8,157,794 B2 | 4/2012 | Dobak, III et al. |
| 8,163,000 B2 | 4/2012 | Dobak, III et al. |
| 8,172,889 B2 | 5/2012 | Yon et al. |
| 8,192,392 B2 | 6/2012 | Solar et al. |
| 8,221,447 B2 | 7/2012 | Solar et al. |
| 8,323,324 B2 | 12/2012 | Magers et al. |
| 8,328,962 B2 | 12/2012 | Schussler |
| 8,343,097 B2 | 1/2013 | Pile-Spellman et al. |
| 8,343,202 B2 | 1/2013 | Magers |
| 8,361,106 B2 | 1/2013 | Solar et al. |
| 8,721,592 B2 | 5/2014 | Solar et al. |
| 8,900,185 B2 | 12/2014 | Solar et al. |
| 8,979,877 B2 | 3/2015 | Thomas |
| 9,028,442 B2 | 5/2015 | Solar et al. |
| 9,180,043 B2 | 11/2015 | Merrill et al. |
| 9,220,899 B2 | 12/2015 | Cattaneo et al. |
| 9,233,013 B2 | 1/2016 | Cattaneo et al. |
| 9,237,964 B2 | 1/2016 | Keller et al. |
| 9,463,113 B2 | 10/2016 | Pile-Spellman et al. |
| 9,561,120 B2 | 2/2017 | Schubler et al. |
| 9,668,893 B2 | 6/2017 | Cattaneo et al. |
| 9,724,491 B2 | 8/2017 | Solar et al. |
| 9,782,185 B2 | 10/2017 | Solar et al. |
| 9,814,824 B2 | 11/2017 | Gilbert et al. |
| 9,855,157 B2 | 1/2018 | Cattaneo et al. |
| 10,058,449 B2 | 8/2018 | Cattaneo |
| 10,213,542 B2 | 2/2019 | Gilbert |
| 10,265,460 B2 | 4/2019 | Gilbert |
| 10,363,364 B2 | 7/2019 | Pile-Spellman et al. |
| 10,363,393 B2 | 7/2019 | Solar et al. |
| 10,709,588 B2 | 7/2020 | Cattaneo et al. |
| 10,722,683 B2 | 7/2020 | Solar et al. |
| 10,773,009 B2 | 9/2020 | Pile-Spellman et al. |
| 10,786,618 B2 | 9/2020 | Gilbert et al. |
| 10,959,878 B2 | 3/2021 | Wolfertz et al. |
| 11,464,671 B2 * | 10/2022 | Berez .................. A61F 7/12 |
| 2002/0091378 A1 | 7/2002 | Dobak, III et al. |
| 2002/0120258 A1 | 8/2002 | Lalonde |
| 2002/0151845 A1 | 10/2002 | Werneth |
| 2002/0151943 A1 | 10/2002 | Balding |
| 2003/0004456 A1 * | 1/2003 | Saab .................. A61M 25/1027 |
| | | 604/96.01 |
| 2004/0167466 A1 * | 8/2004 | Drasler .................. A61F 7/12 |
| | | 604/113 |
| 2011/0276115 A1 | 11/2011 | Merrill |

(56) References Cited

U.S. PATENT DOCUMENTS

| | | | |
|---|---|---|---|
| 2013/0296983 A1 | 11/2013 | Keller et al. | |
| 2014/0025143 A1* | 1/2014 | Atkinson | A61M 1/3613 607/105 |
| 2017/0095649 A1 | 4/2017 | Vase et al. | |
| 2017/0265924 A1 | 9/2017 | Kochavi | |

FOREIGN PATENT DOCUMENTS

| | | |
|---|---|---|
| EP | 3628279 A1 | 4/2020 |
| JP | S593173 U | 1/1984 |
| JP | 2002538857 A | 11/2002 |
| JP | 2006513770 A | 4/2006 |
| JP | 2006524105 A | 10/2006 |
| WO | 2000010494 A1 | 3/2000 |
| WO | 2004075796 A1 | 9/2004 |
| WO | 2018187776 A1 | 10/2018 |

* cited by examiner

THERAPEUTIC ORGAN COOLING

CROSS-REFERENCE TO RELATED APPLICATIONS

The present application is a continuation of U.S. patent application Ser. No. 16/594,112, filed Oct. 7, 2019, which is a continuation of PCT Patent Application PCT/US2018/026600, filed Apr. 6, 2018, which claims priority to U.S. Provisional Patent Application 62/483,294, filed Apr. 7, 2017, all of which are incorporated herein by reference in their entireties.

BACKGROUND

Hypothermia is a promising therapeutic option for patients suffering a lack of oxygen supply to an organ, e.g., due to reduced blood flow. Brain ischemia during acute thromboembolic stroke is an example.

SUMMARY OF INVENTION

Certain embodiments of the disclosure provide tissue cooling devices comprising:
an elongate member having a fluid delivery lumen extending therethrough to a distal port and being sized and configured to extend within a blood vessel; a thermal member extending along at least a portion of the elongate member and having a fluid chamber through which a circulating first fluid flows when in use, thereby cooling a second fluid flowing through the fluid delivery lumen and out the distal port; and a cooling unit that comprises (i) a refrigeration element that cools the first fluid and (ii) a pump for circulating the first fluid through the fluid chamber.

Certain embodiments of the disclosure provide methods of protecting tissue, comprising: introducing a fluid at a location in a lumen of an artery, the location being downstream from an occlusion in the artery, the fluid being cooler than blood in the artery.

BRIEF DESCRIPTION OF THE DRAWINGS

FIG. 1A shows the distal end of the guidewire 105 approaching the occlusion 103 at a location upstream 104 of the occlusion 103 and close to where the occlusion 103 contacts the inner vessel wall 102 of the artery 101.

FIG. 1B shows the distal end of the guidewire passing around the occlusion 103 between the occlusion 103 and the inner vessel wall 102 of the artery 101, and reaching to a location downstream 107 of the occlusion 103 in the artery 101.

FIG. 1C shows a catheter 106 covering the guidewire 105 from a proximate end of the guidewire 105 to close to the distal end of the guidewire 105, passing around the occlusion 103 between the occlusion 103 and the inner vessel wall 102 of the artery 101, and reaching to a location downstream 107 of the occlusion 103 in the artery 101.

FIG. 1D shows the guidewire 105 pulled out of the lumen of the catheter 106, and a cooler liquid being introduced through the catheter 106 to a location downstream 107 of the occlusion 103 in the artery 101.

DETAILED DESCRIPTION

Whole body cooling is often used to achieve hypothermia. However, this produces adverse side effects affecting almost all organ systems, leading potentially to cardiovascular dysfunction, immunosuppression, coagulation impairment, electrolyte imbalances, and acid/base disorders. Additionally, whole body cooling requires more time and thermal energy to reach a target temperature at a target site than would more localized body cooling.

Skin surface cooling methods such as cold rubbing, ice pads, cooling helmets, and cooling coils have been used to reduce temperature locally, but it may require at least 2 hours to reach target temperatures beneath the surface of the skin, with no necessary temperature reduction at an ischemic tissue, e.g., deep in the brain.

There is a need to develop a localized body cooling method to result in fast and selective hypothermia at an ischemic tissue, e.g., affected by vascular occlusion, with reduced effect to core body temperature and to avoid systemic side effects of generalized hypothermia.

Some neuroprotective effects of hypothermia can be attributed to a reduction in oxygen demand. A decrease in brain temperature by 1° C. lowers cerebral oxygen consumption by ~5%, thus increasing tolerance to ischemic conditions. Additionally, cooling the brain may stop or decrease some of the inflammatory and other changes initiated by the ischemia. Similarly, hypothermia can be beneficial to other ischemic tissue affected by a vascular occlusion, e.g., slowed tissue damage and improved recovery of the patient. The methods and apparatus provided herein may be used for localized body cooling to result in fast and selective hypothermia at target ischemic tissue to protect and/or improve recovery of the ischemic tissue.

Provided herein are methods comprising introducing a fluid at a location in a lumen of an artery in a subject (e.g., human, mammals), the location being downstream of an occlusion (e.g., a thrombus, or clot) in the artery, and the fluid being cooler than a blood temperature in the artery. In certain embodiments, the method further comprises: before the introducing, passing within the lumen of the artery a distal end of an elongate member from a location upstream of the occlusion to a location downstream of the occlusion in the lumen of the artery. In certain embodiments, damage to ischemic tissue downstream of the occlusion is reduced or slowed down due to the hypothermia resulting from the introducing of the fluid cooler than the blood temperature in the artery.

Provided herein are also methods comprising introducing a fluid at a location in a lumen of a vein in a subject (e.g., human, mammals), the location being upstream of an occlusion in the vein, and the fluid being cooler than the blood temperature in the vein. In certain embodiments, the method further comprises: before the introducing, passing within the lumen of the vein a distal end of an elongate member from a location downstream of the occlusion to the location upstream of the occlusion in the lumen of the vein. In certain embodiments, damage to ischemic tissue upstream of the occlusion is reduced or slowed down due to the hypothermia resulted from the introducing of the fluid cooler than the blood temperature in the vein.

As used herein, an "occlusion" is a partial or total obstruction, e.g., of a blood vessel, such as an artery or vein.

As used herein, "hypothermia" means that a tissue or organ temperature (e.g., of ischemic tissue) in a subject is at least 1° C. lower than core temperature or than blood temperature in a vein or artery of the subject. A localized hypothermia can be beneficial for protecting tissues. For example, a woman survived without brain damage after being trapped under ice for over an hour, when her core temperature reportedly dropped to about 13.7° C.

A person skilled in the art, such as a medical practitioner, would be able to achieve local hypothermia beneficial to a subject treated by adjusting or choosing the temperature of cold fluid introduced into the subject's blood vessel based on one or more of various factors, e.g., the flow rate of the cool fluid introduced; the composition of the cool fluid introduced; the size, location, and metabolic rate of any ischemic tissue that may benefit from hypothermia; the location and anatomy of the occluded vessel; the rapidity of induction of hypothermia; the patient's physical condition; and other comorbidities.

In certain embodiments of the methods disclosed herein, the fluid introduced has a temperature of about 2° C. to about 35° C., about 2° C. to about 30° C., about 4° C. to about 17° C., about 5° C. to about 30° C., about 5° C. to about 25° C., about 10° C. to about 33.9° C., about 10° C. to about 20° C., about 10° C. to about 15° C., about 32° C. to about 34° C., about 33° C. to about 35° C., or about 14° C. In certain embodiments, the fluid temperature is about 1° C. to about 2° C., about 1° C. to about 10° C., about 1° C. to about 15° C., about 1° C. to about 28° C. from the blood temperature of the artery or vein. In certain embodiments, the fluid is introduced until completion of a thrombectomy or other appropriate procedure for removal of the occlusion. In some embodiments, the fluid is introduced for an extra 30-60 minutes, 1-3 hours, 6-12 hours 12-24 hours, 1-3 days, or other period depending on patient response or other factors. In certain embodiments, the fluid is introduced as soon as possible after symptoms or signs of the occlusion occur, e.g., within about 1, 2, or 4 hours, within about 6-12 hours, within about 12-24 hours, within about 1-3 days, or within 7 days after symptoms or signs of the occlusion occur.

As used herein, "catheter" has its ordinary meaning and can include any elongate structure, such as a tubular member, configured to transmit fluid or objects through a conduit extending along at least a portion of the catheter's length. A catheter may have any of many cross sectional shapes, such as round or polygonal and may resemble a tube, ribbon, etc. As used herein, "guide wire" (or "guidewire") has its ordinary meaning and can include any elongate structure, such as metallic and/or polymeric member, configured to extend into a body viscus or vessel to facilitate access to a location in the body by a catheter or other device. A guide wire may have any of many cross sectional shapes, such as round or polygonal and may resemble a wire, ribbon, rope, or other object.

Figure 2:
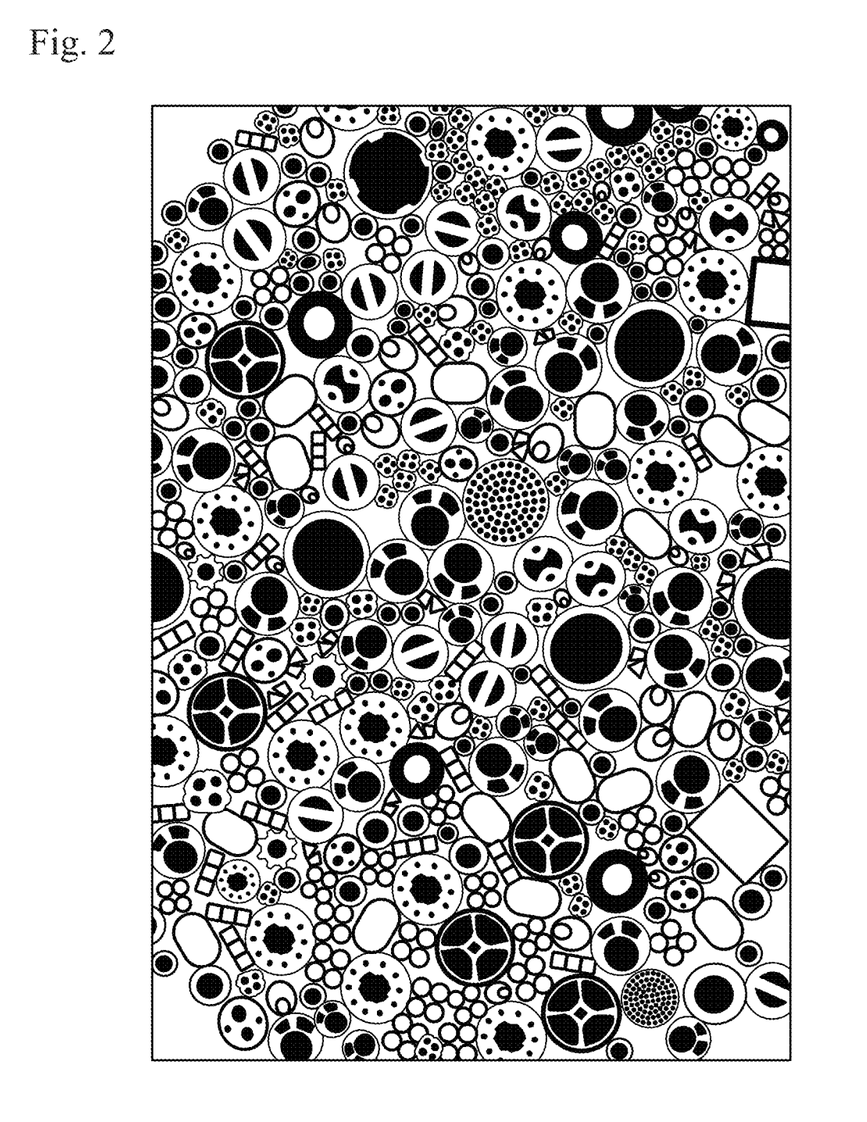
FIG. 2 shows examples of catheters having various configurations with one or more lumens.

In certain embodiments of the methods disclosed herein, the introducing the fluid is through a catheter, an elongate member passing the occlusion. In certain embodiments, the introducing the fluid is through a second elongate member (catheter), different from the first elongate member passing the occlusion (a guide wire). In certain embodiments, the catheter may comprise a plurality of lumens (see, e.g., examples shown in FIG. 2) for introducing different fluids, and/or introducing other accessories as desired, e.g., guidewire, an expandable element (e.g., balloon, also referred to herein as an expandable member), stent, drilling element (e.g., by ultrasound), imaging element, retrieval element, cooling element (also referred to as a thermal member herein), thermally insulate element, sensor element, and any combinations thereof, as described in this disclosure.

The cooling catheter of the disclosure is, in some embodiments, placed intra-arterially with its distal tip in the internal carotid artery (ICA). This provides a thermally insulated conduit to the ICA. The cooling catheter may be flushed with cold flush solution during the procedure.

Figure 1A:
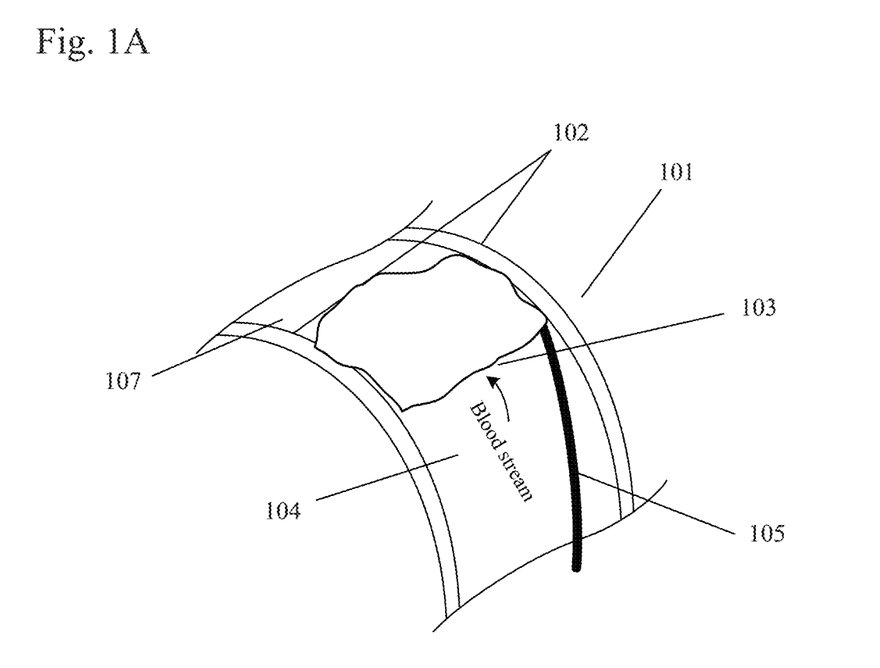
FIGS. 1A-1D show an embodiment of methods disclosed in this disclosure, introducing a cooler fluid at a location in a lumen of an artery 101 that is downstream 107 of an occlusion 103 in the artery 101 by passing around the occlusion 103 a distal end of a guidewire 105 first, then followed by passing through the occlusion 103 a distal end of a catheter 106 for introducing the cooler fluid at the location in the lumen of the artery 101 that is downstream 107 of the occlusion 103.
Figure 1B:
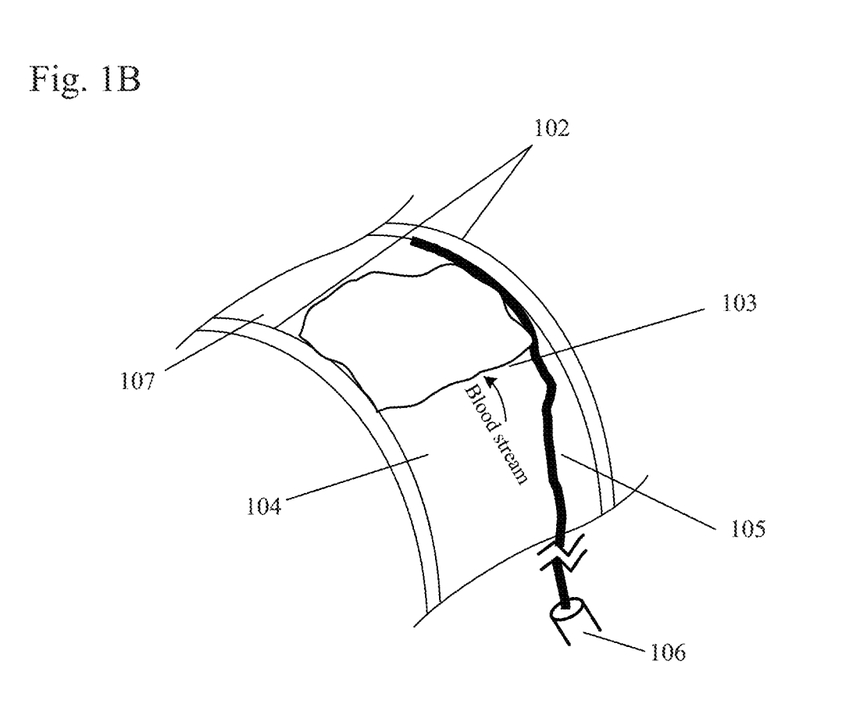
Figure 1C:
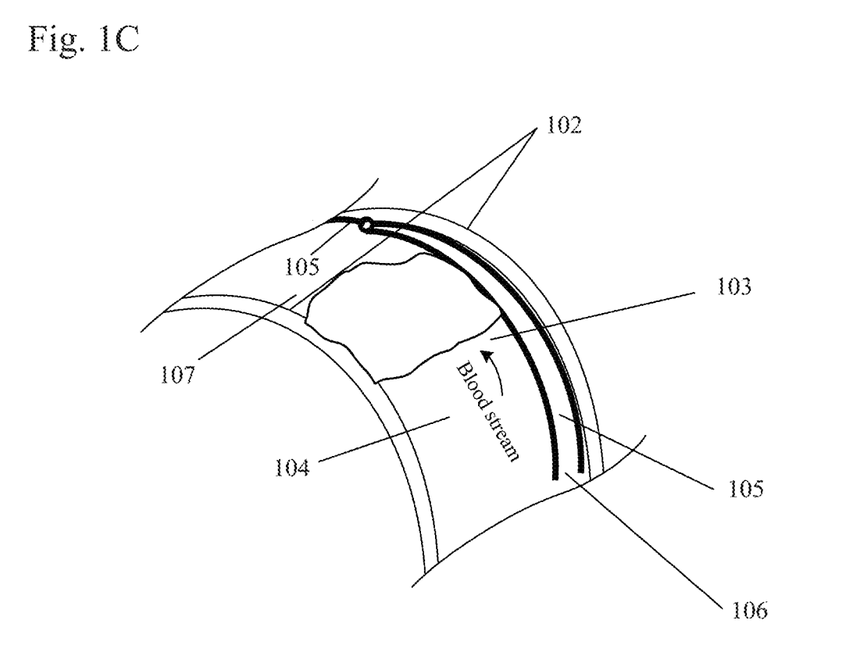
Figure 1D:
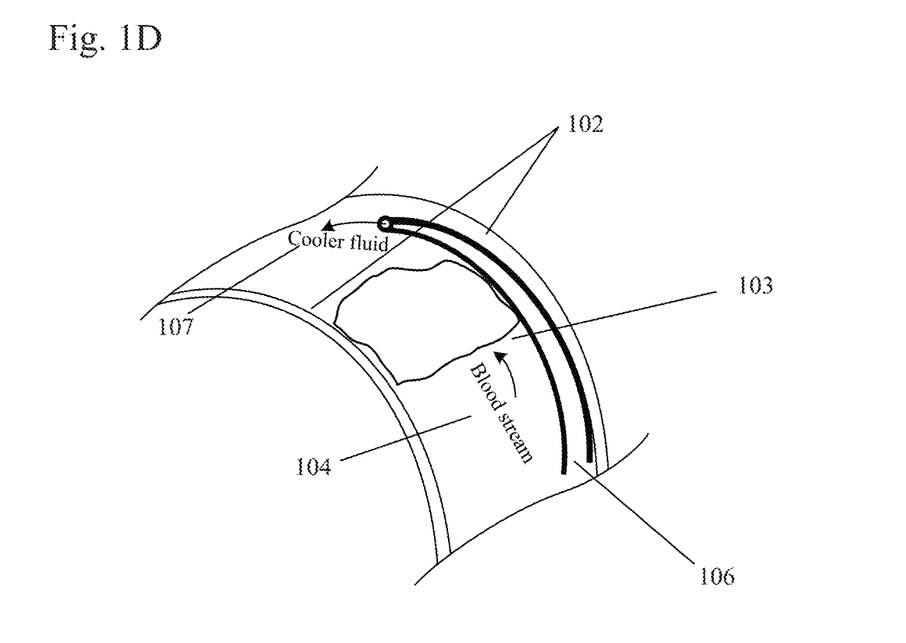

FIGS. 1A-1D show an embodiment of the methods disclosed herein. FIG. 1A shows an occlusion 103 in a lumen of an artery 101 having a vessel wall 102, a distal end of a guidewire 105 approaches the occlusion 103 in the lumen 104 of the artery 101 from the upstream 104 of the occlusion 103 at where the occlusion 103 contacts the inner vessel wall 102. FIG. 1B shows the distal end of the guidewire 105 passing around the occlusion 103 to a location downstream 107 of the occlusion 103 by passing between the occlusion 103 and the inner vessel wall 102. A catheter 106 is applied over the guidewire 105 from a location close to a proximate end of the guidewire 105 (FIG. 1B), until the catheter 106 passes around the occlusion 103 between the occlusion 103 and the inner vessel wall 102 to reach to a location downstream 107 of the occlusion 103 in the lumen 104 of the artery 101 (FIG. 1C). The guidewire 105 is pulled out of the catheter 106, and a cooler liquid that has a temperature cooler than the blood temperature of the artery is introduced to the location downstream 107 of the occlusion 103 (FIG. 1D).

In certain embodiments of the methods disclosed herein, the passing includes passing through or around a portion of the occlusion. In certain embodiments, the elongate member comprises a penetrating element (e.g., an element with a blunt or sharp distal end, and/or with a drilling element at the distal end) passing through or around the portion of the occlusion. The penetrating element may be pulled out from the catheter after the passing step such that the fluid can be introduced through the elongate member. For catheters having a plurality of lumens, the penetrating element may not need to be pulled out before the introducing the fluid, as the fluid may be introduced through a different lumen.

In certain embodiments of the methods disclosed herein, the method further comprises utilizing the one or more lumens of the catheter, and/or one or more accessories for one or more tasks these lumens and/or accessories may be used for. For example, the method may further comprise one or more steps of retrieving the occlusion via the retrieval element, providing image of the location downstream of the occlusion of an artery or upstream of the occlusion of a vein, detecting one or more parameters of the location downstream of the occlusion of an artery or upstream of the occlusion of a vein by one or more sensor elements, and cooling the fluid until it is introduced to the desired location.

In certain embodiments of the methods disclosed herein, the passing includes passing around the occlusion, e.g., between the occlusion and the vessel wall of the artery or vein. In certain embodiments, the elongate member comprises a guidewire that passes between the occlusion and the vessel wall of the artery or vein. The elongate member may be a catheter comprising one or more lumens. The guidewire may be pulled out from the catheter such that the fluid can be introduced through the catheter. For catheters having a plurality of lumens, the guidewire may not need to be pulled out before the introducing the fluid, as the fluid may be introduced through a different lumen.

In certain embodiments of the methods disclosed herein, a catheter may be configured to comprise an expandable element (e.g., balloon) close to the distal end of the catheter, and the method further comprises expanding the expandable element after the distal end of the elongate member and the expandable element are positioned at a desired location. The expandable element can occlude the blood vessel for flow arrest while introducing the cooler fluid.

In certain embodiments of the methods disclosed herein, the occlusion can be removed by a retrieval element the catheter is configured with, either immediately or after having first cooled the ischemic tissue to the desired therapeutic hypothermic temperature. For example, the retrieval element may be positioned adjacent to an occluding thrombus and retrieve the thrombus. Examples of retrieval elements include, without limitation, a thrombectomy device (e.g., Solitaire® revascularization device), basket, wire, or atherectomy device.

In certain embodiments of the methods disclosed herein, the fluid is cooled extracorporeally. In certain embodiments, the fluid is cooled or maintained at a temperature lower than the blood temperature of the subject treated when a catheter introducing the fluid comprises a cooling mechanism and/or a thermal insulator.

In certain embodiments of the methods disclosed herein, the fluid comprises an intravenous solution. Examples of the intravenous solutions include, without limitation, colloid solutions, crystalloids, and blood products such as serum or plasma. Further examples of the colloid solutions include, without limitation, albumin (e.g., 5% or 25%), hetastarch (hespan), dextran. Examples of the crystalloid solutions include, without limitation, normal saline, half normal saline, lactate ringers, and dextrose 5%, D5 half-normal saline. In certain embodiments, the fluid may further comprise additional oxygen dissolved therein.

In certain embodiments of the methods disclosed herein, the fluid further comprises one or more active ingredients (AI) for therapeutic and/or diagnostic purposes. Examples of the AI may include thrombolytic agents such as tissue plasminogen activator (tPA), streptokinase, or urokinase. The AI may slow down apoptosis and/or metabolism of ischemic tissue either downstream of the occlusion in an artery or upstream of the occlusion in a vein. For example, kinase inhibitors (e.g., tyrosine kinase inhibitors, GSK-3 inhibitors, PI3-kinase gamma inhibitors), monocarboxylate tranporter (MCT) inhibitors may be used. AIs may also include osmotic agents such as mannitol (e.g., 20% mannitol) to reduce intracranial pressure, and any combinations of agents or classes of agents.

In certain embodiments of the methods disclosed herein, the occlusion in the artery or vein can include a thrombus, dissection, atheromatous plaque, embolism (by air, fat, foreign body, thrombus), or any combinations thereof. The organs the occlusion in the artery or vein may affect include, without limitation, brain (e.g., thrombotic or thromboembolic stroke, certain cases of hemorrhagic stroke, traumatic brain injury, and iatrogenic injury during interventional procedures), heart, lung, limbs, liver, pancreas, spleen, and kidney.

There is a limitation in delivering cold fluid to a lesion site. Cold fluid injected in the hub of a regular catheter that is placed in warm, flowing blood is warmed by the time it reaches the tip of the catheter. Provided herein are catheters comprising a lumen for introducing the cooler fluid to a location desired as described in the methods herein.

In certain embodiments, the catheter comprises a delivery lumen through which the cooler fluid travels through until introduced to a desired location as described herein. In certain embodiments, the delivery lumen is thermally insulated (a thermally insulated lumen), which reduces the temperature change of the fluid traveling through. Thereby, the cooler fluid exiting from the distal end of the delivery lumen can cool down at least a portion of the tissue the cooler fluid contacts. In certain embodiments, the tissue is in a brain, heart, lung, limbs, or kidney, and such delivery of cooler fluid as disclosed herein may lower the temperature of the organ and induce therapeutic hypothermia to the ischemic tissue affected by the artery with the occlusion.

In certain embodiments, the catheter comprises a cooling element not only reducing the temperature gain of a cooler fluid traveling through, but also further lowering the temperature of the fluid. The cooling element may comprise a heat transfer medium circulation system, wherein a heat transfer medium is circulated to provide heat exchange through the inside wall of the catheter where the fluid travels through. The cooling element may comprise a compressed air cooling system or any other cooling system that can implement the desired heat exchange with the fluid.

For example, the cooling element can surround a substantial portion of the delivery lumen of the catheter that is close to the distal end of the catheter and is in contact with blood in the blood vessel the catheter travels through. The cooling element comprises a plurality of ports for a plurality of lumens in desired fluid communication for circulation with a chiller unit providing cooler heat transfer media, a cooler media suitable for heat transfer can be introduced into the cooling element from one or more of the ports, then travels through the corresponding lumens until exiting the cooling element from one or more of the ports. The fluid traveling through the delivery lumen is cooled or maintained cool when in heat transfer with the cooler heat transfer media circulated in the plurality of lumens of the cooling element.

In certain embodiments, the catheter further comprises an expandable element close to its distal end such that once the expandable element passes through the occlusion as described herein, it has a diameter larger than the majority section of the catheter from its proximate end. The larger diameter of the expandable element prevents the fluid introduced through the catheter from backflow. For example, the largest diameter of the expandable element may be about 2 to about 10 times larger, about 2 to about 15 times, or about 2 to about 20 times larger than the diameter of the catheter section immediate following the expandable element.

In certain embodiments, the expandable element expands after passing through the occlusion as described herein. Examples of expandable elements include, without limitation, balloons.

Figure 3:
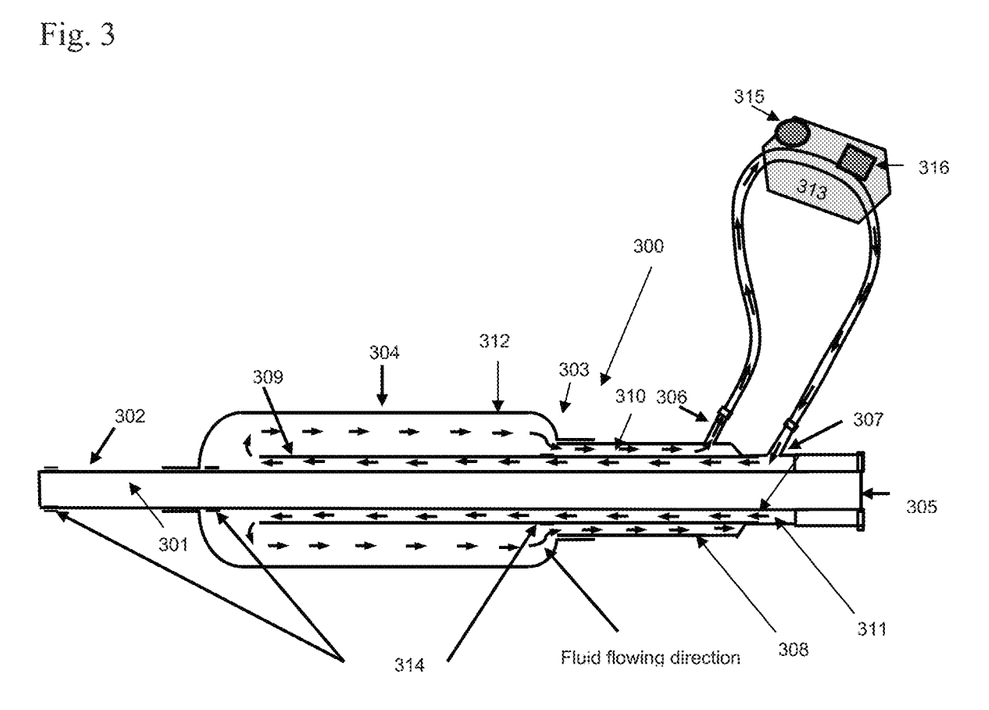
FIG. 3 shows an embodiment of a cooling catheter 300, having a heat transfer media injected into the inner lumen 311 and returned via the outer lumen 310.
Figure 4:
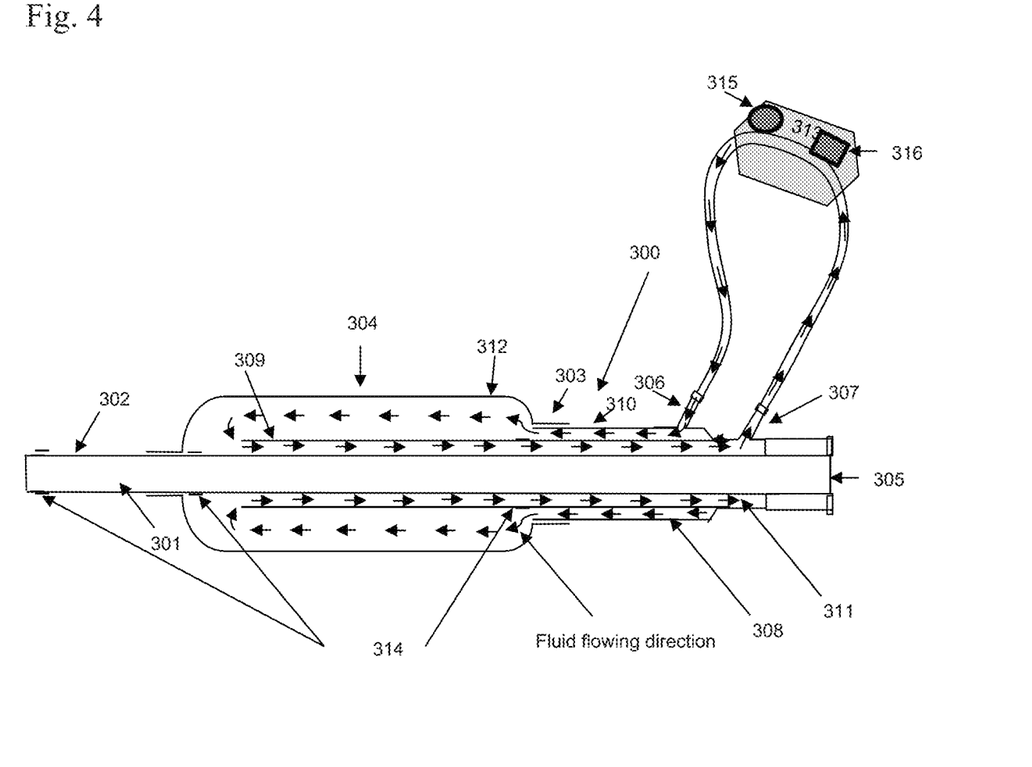
FIG. 4 shows an embodiment of a cooling catheter, having a heat transfer media injected into the outer lumen 310 and returned via the inner lumen 311.

FIGS. 3 and 4 show embodiments of an elongate member (a cooling catheter 300) comprising a delivery lumen 301 defined by a delivery shaft 302, a cooling element 303 further comprising an expandable element, such as a balloon 304, a fluid delivery port 305 for introducing the cooler fluid to the delivery lumen 301, and two heat transfer media ports 306 and 307 close to the proximal end of the cooling element 303 allowing the heat transfer media to enter and exit the cooling element 303. The cooling element 303 comprises an outer shaft 308 surrounding the delivery shaft 302 for a substantial portion close to the distal end, and an inner shaft 309 spaced between the outer shaft 308 and the delivery shaft 302 to divide the fluid chamber between the outer shaft 308 and the delivery shaft 302 into two lumens in fluid communication: the outer lumen 310 between the outer shaft 308 and the inner shaft 309, and the inner lumen 311 between the inner shaft 309 and the delivery shaft 302. The inner shaft 309 does not extend between the outer shaft 308 and the delivery shaft 302 all the way to the distal end of the cooling element 303, thus to allow the outer lumen 310 and inner lumen 311 to be fluid communicated. The heat transfer media may enter the outer lumen 310 through the port 306, then exit through the inner lumen 311 and the port 307, as shown in FIG. 3. Alternatively, the heat transfer media may enter the inner lumen 311 through the port 307, then exit through the outer lumen 310 and the port 306, as shown in FIG. 4. The ports 306 and 307 may be connected to a cooling/chiller unit 313 that may provide and circulate cooler heat transfer media. The cooling/chiller unit 313 may include a pump 315 for circulating the heat transfer media through the fluid chamber and a refrigeration element 316 that cools the heat transfer media. The outer shaft 308 comprises at least two sections with different diameters, a larger diameter section (balloon shaft 312) close to the distal end of the cooling element 303 that defines the balloon 304, and a section with smaller diameter(s) close to the proximal end of the cooling element 303. The larger diameter section (balloon shaft 312) has the largest diameter of the outer shaft 308. The balloon may be expandable and expands at a desired location (e.g., after the proximate end of the balloon 304 passes around or through the occlusion in an embodiment of the methods disclosed herein). The thermal member 303 optionally may further comprise one or more radiopaque markers 314 marking the distal end of the delivery lumen 301, the distal end and proximal end of the balloon 304 to assist physicians to position and track the delivery lumen 301 and the balloon 304.

The balloon 304 may be made of compliant, semi-compliant, or non-compliant material. For low-profile shaft design, a compliant balloon may be preferable.

Materials suitable for the delivery shaft 302, inner shaft 309 and outer shaft 308 include, without limitation, composite reinforced shaft, multi stiffness polymer shafts, metal (laser cut) hypotube shaft jacket with polymer materials.

In certain embodiments, the cooling catheter 300 shown in FIGS. 3 and 4 may further comprise a smaller balloon (as an additional expandable element) at the distal tip of the delivery lumen 301 which can be expanded (e.g., inflated) to occlude the blood vessel (flow arrest) with additional injection port to expand and deflate the balloon.

In certain embodiments, a distal access catheter may be placed through the delivery lumen, e.g., the distal access catheter may be essentially a large bore (e.g. 5 or 6F catheter about 0.045" to 0.07" ID) with its tip going more distal. If the tip of the distal access catheter can reach the occlusion (e.g., thrombus) it can potentially be used as an aspiration catheter to remove the occlusion. The distal access catheter can be flushed with the cooler fluid.

Through the delivery lumen of the distal access catheter, a microcatheter (e.g., 0.021 or 0.027" ID) can be passed over a guide wire and the tip of the microcatheter can be advanced carefully past the occlusion. Once the distal end of the distal access or the delivery lumen is positioned in a desired location in the blood vessel, cooling of the tissues affected by the occlusion (e.g., ischemic parenchyma) can begin immediately by introducing the cooler fluid as disclosed herein, even before attempted removal of the occlusion and restoration of flow. Cooling the ischemic tissue prior to the restoration of the flow of oxygenated blood may decrease reperfusion injury. The ischemic tissue will be cooled by infusion of cooler fluid as disclosed herein, which may increase oxygen carrying capacity (e.g., by blood or artificial heme) and/or include AIs as disclosed herein to decrease the size of the infarct.

Additionally, a retrieval device as described herein may be brought adjacent to the occlusion by passing through the lumen of a microcatheter, then unsheathing or otherwise deploying the retrieval device, and retrieving the occlusion.

Examples

Method 1. A method of protecting tissue, comprising: introducing a fluid at a location in a lumen of an artery, the location being downstream from an occlusion in the artery, the fluid being cooler than blood in the artery.

Method 2. The method according to method 1, further comprising: before the introducing, passing within the lumen an end of an elongate member from a location upstream from the occlusion to a location downstream from the occlusion.

Method 3. The method according to method 2, wherein the elongate member comprises a guide wire.

Method 4. The method according to method 2 or 3, wherein the introducing the fluid is through a catheter having a distal end placed in a location downstream from the occlusion.

Method 5. The method according to method 2, 3, or 4, wherein the end of the elongate member is passed to the location downstream from the occlusion by passing around the occlusion.

Method 6. The method according to any one of methods 2-5, further comprising expanding an expandable element that limits the fluid introduced to the downstream location from flowing upstream from the occlusion.

Method 7. The method according to any one of methods 4-5, wherein the catheter comprises a thermal insulation element to keep the fluid cool until it is introduced to the location downstream.

Method 8. The method according to any one of methods 1-7, wherein the occlusion comprises a thrombus, and further comprising retrieving at least a portion of a thrombus from the artery.

Method 9. The method according to any one of methods 1-8, wherein the fluid has a temperature of about 2° C. to about 35° C.

Method 10. The method according to any one of methods 1-9, wherein the fluid has a temperature of about 5° C. to about 30° C.

Method 11. The method according to any one of methods 1-10, wherein the fluid has a temperature of about 10° C. to about 25° C.

Method 12. The method according to any one of methods 1-11, wherein the fluid has a temperature of about 10° C. to about 20° C.

Method 13. The method according to any one of methods 1-12, the fluid has a temperature of about 15° C.

Method 14. The method of any one of methods 1-13, wherein the location the fluid being introduced is in an internal carotid artery (ICA), or branches thereof (e.g., MCA, ACA, and their branches).

Method 15. The method of any one of methods 1-14, further comprising introducing cooling fluid into artery after the thrombus is removed.

Apparatus 1. A tissue cooling device comprising: an elongate member having a fluid delivery lumen extending therethrough to a distal port and being sized and configured to extend within a blood vessel; a thermal member extending along at least a portion of the elongate member and having a fluid chamber through which a circulating first fluid flows when in use, thereby cooling a second fluid flowing through the fluid delivery lumen and out the distal port; and a cooling unit that comprises (i) a refrigeration element that cools the first fluid and (ii) a pump for circulating the first fluid through the fluid chamber.

Apparatus 2. The tissue cooling device of Apparatus 1, further comprising an expandable member coupled to a distal portion of the elongate member, the expandable member configured to expand within and at least partially occlude the blood vessel.

Apparatus 3. The tissue cooling device of Apparatus 2, wherein the thermal member comprises the expandable member, and the circulating first fluid expands the expandable member.

Multiple embodiments have been shown and described. Various changes and substitutions may of course be made without departing from the spirit and scope of the invention. The invention, therefore, should not be limited, except by the following claims and their equivalents.

The invention claimed is:

1. A method of protecting tissue, comprising:
   providing a tissue cooling device comprising:
   an elongate member having a fluid delivery lumen extending therethrough to a distal port and being sized and configured to extend within a blood vessel;
   a thermal member extending along at least a portion of the elongate member and having a fluid chamber through which a circulating first fluid flows when in use, thereby cooling a second fluid flowing through the fluid delivery lumen and out the distal port; and
   a cooling unit in fluid communication with the fluid chamber at a proximal region of the device and that comprises (i) a refrigeration element that cools the first fluid and (ii) a pump for circulating the first fluid through the fluid chamber,
   wherein the fluid chamber is divided into an outer lumen and an inner lumen in fluid communication with the outer lumen, the inner lumen extending alongside a length of the elongate member and being closer to the fluid delivery lumen than is the outer lumen,
   wherein the device is configured such that, in use, the circulating first fluid flows from the cooling unit into and through the outer lumen in a direction from proximal to distal, then flows into and through the inner lumen in a direction from distal to proximal alongside and in thermal communication with the fluid delivery lumen,
   wherein the device is configured to introduce the second fluid from a proximal end of the elongate member through the distal port when the distal port is positioned in a lumen of an artery, the second fluid being cooler than blood in the artery, such that, when the device is in use, the second fluid passing out of the distal port of the fluid delivery lumen cools blood in the artery, and
   wherein the device is thermally insulated from blood in the artery; and
   introducing the second fluid into the fluid delivery lumen and to a location in a lumen of an artery, the location being downstream from an occlusion in the artery, the second fluid being cooler than blood in the artery;
   wherein the second fluid passes out of the distal port of the fluid delivery lumen and cools blood in the artery; and
   wherein the device is thermally insulated from blood in the artery.

2. The method of claim 1, wherein the elongate member is a first elongate member, and further comprising: before the introducing, passing within the lumen an end of a second elongate member from a location upstream from the occlusion to a location downstream from the occlusion.

3. The method of claim 2, wherein the second elongate member comprises a guide wire.

4. The method of claim 2, wherein the introducing the second fluid is through a catheter having a distal end placed in a location downstream from the occlusion.

5. The method of claim 4, further comprising expanding an expandable element that limits the fluid introduced to the downstream location from flowing upstream from the occlusion.

6. The method of claim 4, wherein the catheter comprises a thermal insulation element to keep the fluid cool until it is introduced to the location downstream.

7. The method of claim 2, wherein the end of the second elongate member is passed to the location downstream from the occlusion by passing around the occlusion.

8. The method of claim 1, wherein the occlusion comprises a thrombus, and further comprising retrieving at least a portion of a thrombus from the artery.

9. The method of claim 8, further comprising introducing cooling fluid into artery after the thrombus is removed.

10. The method of claim 1, wherein the fluid has a temperature of about 2° C. to about 35° C.

11. The method of claim 1, wherein the fluid has a temperature of about 5° C. to about 30° C.

12. The method of claim 1, wherein the fluid has a temperature of about 10° C. to about 25° C.

13. The method of claim 1, wherein the fluid has a temperature of about 10° C. to about 20° C.

14. The method of claim 1, wherein the fluid has a temperature of about 15° C.

15. The method of claim 1, wherein the location the fluid is introduced is in an internal carotid artery, or branches thereof.

* * * * *